(12) United States Patent
Keller et al.

(10) Patent No.: US 7,267,691 B2
(45) Date of Patent: *Sep. 11, 2007

(54) CERVICAL INTERVERTEBRAL PROSTHESIS

(75) Inventors: Arnold Keller, Kayhude (DE); Paul C. McAfee, Baltimore, MD (US)

(73) Assignee: Cervitech, Inc., Rockaway, NJ (US)

( * ) Notice: Subject to any disclaimer, the term of this patent is extended or adjusted under 35 U.S.C. 154(b) by 32 days.

This patent is subject to a terminal disclaimer.

(21) Appl. No.: 10/349,183

(22) Filed: Jan. 23, 2003

(65) Prior Publication Data
US 2004/0083000 A1    Apr. 29, 2004

(30) Foreign Application Priority Data
Mar. 12, 2002   (EP)   ................................. 02005631

(51) Int. Cl.
*A61F 2/44* (2006.01)
(52) U.S. Cl. .................................. 623/17.14
(58) Field of Classification Search ............. 623/11.11, 623/16.11, 17.11–17.16, 23.5, 23.53, 23.57, 623/23.55; 606/60, 61
See application file for complete search history.

(56) References Cited

U.S. PATENT DOCUMENTS

| | | | | |
|---|---|---|---|---|
| 4,349,921 A | * | 9/1982 | Kuntz ....................... | 623/17.16 |
| 5,236,460 A | * | 8/1993 | Barber ...................... | 623/17.15 |
| 5,258,031 A | * | 11/1993 | Salib et al. ............... | 623/17.15 |
| 5,306,307 A | | 4/1994 | Senter et al. | |
| 5,360,430 A | * | 11/1994 | Lin .............................. | 606/61 |
| 5,425,773 A | * | 6/1995 | Boyd et al. ............... | 623/17.15 |
| 5,534,029 A | * | 7/1996 | Shima ...................... | 623/17.15 |
| 5,865,848 A | * | 2/1999 | Baker ....................... | 623/17.15 |
| 6,063,121 A | * | 5/2000 | Xavier et al. ............. | 623/17.15 |
| 6,136,001 A | * | 10/2000 | Michelson .................... | 606/61 |
| 6,146,421 A | * | 11/2000 | Gordon et al. ........... | 623/17.15 |
| 6,156,067 A | * | 12/2000 | Bryan et al. .............. | 623/17.15 |
| 6,174,311 B1 | * | 1/2001 | Branch et al. ................. | 606/61 |
| 6,190,414 B1 | * | 2/2001 | Young et al. ............. | 623/17.15 |
| 6,228,118 B1 | * | 5/2001 | Gordon .................... | 623/17.14 |
| 6,517,580 B1 | * | 2/2003 | Ramadan et al. ........ | 623/17.15 |

(Continued)

FOREIGN PATENT DOCUMENTS

DE    295 11 146    1/1996

(Continued)

*Primary Examiner*—Anu Ramana
(74) *Attorney, Agent, or Firm*—Morrison & Foerster LLP

(57) ABSTRACT

A cervical intervertebral prosthesis includes two cover plates which are each configured to be connected to adjacent vertebral bodies. At least one of the two cover plates has a toothed portion which faces toward the vertebral body and whose teeth have a steep, ventrally directed flank and a less steep, dorsally directed flank. When the prosthesis is fitted with sufficient pressing between its adjacent vertebral bodies, the combination of the serrated toothed portion and the abutment surface is sufficient to hold the prosthesis securely in the desired position. In many cases this makes it possible to dispense with additional screw fixation. The flange carrying the abutment surface is in this case expediently shortened so that it can be accommodated in a recess of the bone so that the prosthesis does not protrude ventrally beyond the ventral alignment surface of the adjacent vertebral bodies.

22 Claims, 1 Drawing Sheet

U.S. PATENT DOCUMENTS

| | | | |
|---|---|---|---|
| 6,547,823 B2 * | 4/2003 | Scarborough et al. ... | 623/17.16 |
| 6,610,093 B1 * | 8/2003 | Pisharodi ............ | 623/17.15 |
| 6,635,087 B2 * | 10/2003 | Angelucci et al. ..... | 623/17.11 |
| 7,001,432 B2 * | 2/2006 | Keller et al. ......... | 623/17.14 |
| 2001/0039454 A1 * | 11/2001 | Ricci et al. .......... | 623/23.5 |
| 2003/0105527 A1 * | 6/2003 | Bresina .............. | 623/17.16 |
| 2003/0176923 A1 * | 9/2003 | Keller et al. ......... | 623/17.14 |
| 2004/0102846 A1 * | 5/2004 | Keller et al. ......... | 623/17.11 |

FOREIGN PATENT DOCUMENTS

| | | |
|---|---|---|
| EP | 0 747 025 | 12/1996 |
| FR | 2 718 635 | 10/1995 |
| WO | WO97/20526 | 6/1997 |
| WO | WO99/65412 | 12/1999 |
| WO | WO 00/53127 | 9/2000 |
| WO | WO 01/01893 | 1/2001 |

* cited by examiner

CERVICAL INTERVERTEBRAL PROSTHESIS

FIELD AND BACKGROUND OF THE INVENTION

In the cervical region of the vertebral column, there is only a small amount of space available for receiving intervertebral prostheses. Even a slight shifting of prosthesis parts in the dorsal direction can affect the nerves of the spinal cord. Secure fixation of the prostheses is therefore of great importance. In the case of intervertebral prostheses for the lumbar region of the vertebral column, it is known for the cover plates of the prosthesis which face the adjacent vertebral bodies to be provided with ribs or projections which engage in prepared grooves in the vertebral bodies or are designed to be sharp and self-cutting. This is made possible by the fact that the vertebral bodies of the lumbar vertebral column are relatively large and high, so that there is enough space available for fixation devices of this kind. This also applies to fixation flanges which are provided at the ventral edge of the cover plates of the prostheses in order to receive bone screws for securing the cover plates on the associated vertebral bodies. The smallness and low height of the vertebral bodies in the cervical region often rules out the use of these fixation devices or means that said fixation devices appear unsatisfactory. This is all the more so given that ventrally protruding parts of the prostheses have to be avoided, because these can lead to irritation of the esophagus lying immediately in front of them.

SUMMARY OF THE INVENTION

It is therefore an object of the invention to make available a cervical intervertebral prosthesis with small fixation members which take account of the confined spatial conditions and which nevertheless afford sufficient safety.

The solution according to the invention lies in the basic concept of the use of two fixation means acting against one another, namely, on the one hand, a serrated toothing which cooperates with the bone and which prevents a ventrally directed relative movement of the prosthesis and promotes a dorsally directed relative movement, and, on the other hand, an abutment that definitively limits the dorsally directed relative movement.

At least one of the two cover plates belonging to the prosthesis is provided, on its surface cooperating with the associated vertebral body, with a toothing comprising at least one tooth with a steep, ventrally directed flank and a less steep, dorsally directed flank. This is generally referred to as a serration. The effect of these serrations is that, in the event of a relative movement between the cover plate and the associated vertebral body, a force is exerted on the vertebral body which tends to push it in the dorsal direction. The serrations thus secure against undesired shifting of the cover plate and of the prosthesis in the ventral direction. A multiplicity of such teeth are preferably provided in the toothing. The teeth expediently extend like ribs transversely with respect to the sagittal direction. The toothing should cover substantially the whole surface. At least it should cover approximately half of the available surface directed toward the vertebral body. The teeth must be high enough to be able to exert a sufficient effect. On the other hand, they should be as low as possible in order to take up only a small vertical space. It has proven advantageous if they have a height of between 0.2 and 0.6 mm and if their spacing in the sagittal direction is between 0.5 and 2 mm.

The dorsally directed force which the toothing exerts on the cover plate is effective only upon relative movement between the cover plate and the associated vertebral body. Such a relative movement is undesirable, because in normal circumstances one obviously expects absolute immobilization between the cover plate and the associated vertebral body. In fact, the teeth, which can be regarded as a macroscopic roughening, normally contribute to maintaining the immobilized state between the cover plate and the associated vertebral body. This can be further promoted by providing the prosthesis surface with a coating which promotes intimate connection between bone and prosthesis surface, for example with a microporous and/or bioactive material promoting bone growth.

The force which the toothing exerts in the dorsal direction on the cover plate in the event of a relative movement is neutralized by an abutment surface which is provided at the ventral edge of the cover plate in order to cooperate with the ventral margin of the associated vertebral body. The effect of this abutment surface is that the cover plate, and thus also the prosthesis, can be moved in the dorsal direction by the force of the serrations only until the abutment surface of the cover plate bears against the ventral margin of the vertebral body. The dimensions are chosen such that the desired position of the prosthesis is reached exactly when the abutment surface bears against the ventral margin of the vertebral body.

The abutment surface is expediently formed by a flange which is arranged symmetrically at the ventral edge of the cover plate across a width which is expediently at least as great as half the mediolateral dimension of the cover plate. The result of this is that a parallel bearing of the flange on the ventral margin of the vertebral body is obtained at all times, and an inclined position of the desired sagittal axis of the prosthesis in relation to the sagittal direction of the vertebral body is ruled out.

The flange can be provided with openings for receiving fixation members, for example bone screws. However, in most cases this is not necessary. A design in which there are no such screw holes and in which the flange has a smaller height in order to be able only to exert its abutment function can even be particularly advantageous. This is because it affords the possibility of forming a recess in the vertebral body, which recess receives the flange. The result of this is that the prosthesis can be pushed so far dorsally in relation to the ventral alignment surface of the adjacent vertebral bodies that it cannot cause irritation of the esophagus or of any nerves or vessels extending there. The prosthesis can even remain completely behind this alignment surface and, viewed from the ventral direction, can thus be anchored completely in the area of the vertebral bodies. Doing without the screw holes also has the advantage that the flange can be given such a low height that the implant becomes very small and can be implanted through a narrow access channel, for example of an endoscope.

If the serrations are designed as ribs extending transversely in relation to the sagittal direction, there is a possibility of the cover plate shifting relative to the associated vertebral body in the direction of these ribs. This can be avoided by providing grooves or ribs which extend transversely in relation to the direction of the tooth ribs. The grooves permit ingrowth of bone substance and thereby prevent the undesired transverse movement. Any ribs provided are expediently self-cutting so that they penetrate into the surface of the vertebral body as the prosthesis is inserted.

The abutment surface does not necessarily have to be formed by a flange. Instead, projections oriented transversely in relation to the plane of the cover plates in many cases suffice. These projections should be arranged symmetrically in a pair in order to permit an orientation of the prosthesis coincident with the direction of the vertebral bodies. Forming the abutment surface on a pair of symmetrically arranged projections spaced apart from one another has the advantage that the ventral center area of the vertebral bodies, which in principle is expected to be in proximity to the esophagus, is free from prosthesis parts.

All the ventral margins and edges of the prosthesis should be well rounded-off in order to minimize their potential for possible irritation of adjacent organs.

BRIEF DESCRIPTION OF THE DRAWINGS

The invention is explained in more detail below with reference to the in the drawing which depicts an advantageous illustrative embodiments. In the drawing.

DETAILED DESCRIPTION OF THE INVENTION

Figure 1:
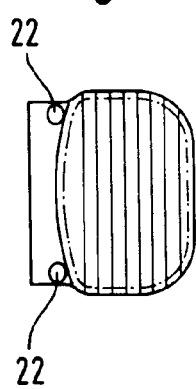
FIG. 1 shows a plan view of the upper end plate of a prosthesis to approximately true scale.

The prosthesis comprises a lower cover plate 1 of hard, resistant material, in particular metal, a prosthesis core 2 made of polyethylene or other plastic which has good sliding properties, and an upper cover plate 3 which is made of the same material as the lower cover plate 1. The prosthesis core 2 is connected to the lower cover plate 1 firmly, albeit also detachably. The connection is effected by undercut ledges 4 on the dorsal side and both lateral sides of the lower cover plate 1, into which the prosthesis core 2 provided with complementary grooves can be pushed. In the pushed-in position, it is secured by a bolt 5. The prosthesis core 2 and the upper cover plate 3 form interacting, complementary, preferably spherical slide surfaces 6.

Those surfaces of the cover plates 1 and 3 each facing the associated vertebral body 7 are designed the same. The greater part of their surface is covered by a multiplicity of teeth 9 which are of serrated design, namely with a steep flank 10 directed toward the ventral side, and with a less steep flank 11 directed toward the dorsal side. The steep flank is preferably approximately perpendicular to the plane of extent of the cover plates.

The teeth 9 are in the form of ribs which extend transversely in relation to the sagittal mid-axis 8 and which are interrupted in the middle to form a groove 12. The teeth 9 are absent in the area of the groove 12. In the example shown, the bottom surface 13 of the groove coincides with the bottom surface of the teeth and is indicated by a broken line in FIG. 3. However, the groove can also be deeper or shallower. Instead of a centrally arranged groove, a plurality of possibly narrower grooves can also be provided, distributed across the surface. A symmetrical arrangement is recommended. After insertion of the prosthesis, and in cooperation with the adjacent bone substance, the lateral end faces of the teeth 9 directed toward the groove generate a resistance to lateral shifting of the prosthesis relative to the bone. This resistance increases, during further use, as a result of the bone substance growing into the groove 12.

Instead of by a groove, this effect can also be generated by one or more ribs which extend transversely in relation to the extent of the ribs forming the teeth 9. These ribs should be narrow and sharp so that, upon insertion of the prosthesis, they can easily penetrate into the bone substance and do not impede the immediate production of a tight fit of the cover plate surface on the respectively associated bone surface.

To promote an intimate contact between prosthesis surface and bone surface, the prosthesis surface can be provided with a coating 14 into whose pores the bone substance grows and/or which biologically promotes the incorporation of bone substance.

Figure 3:
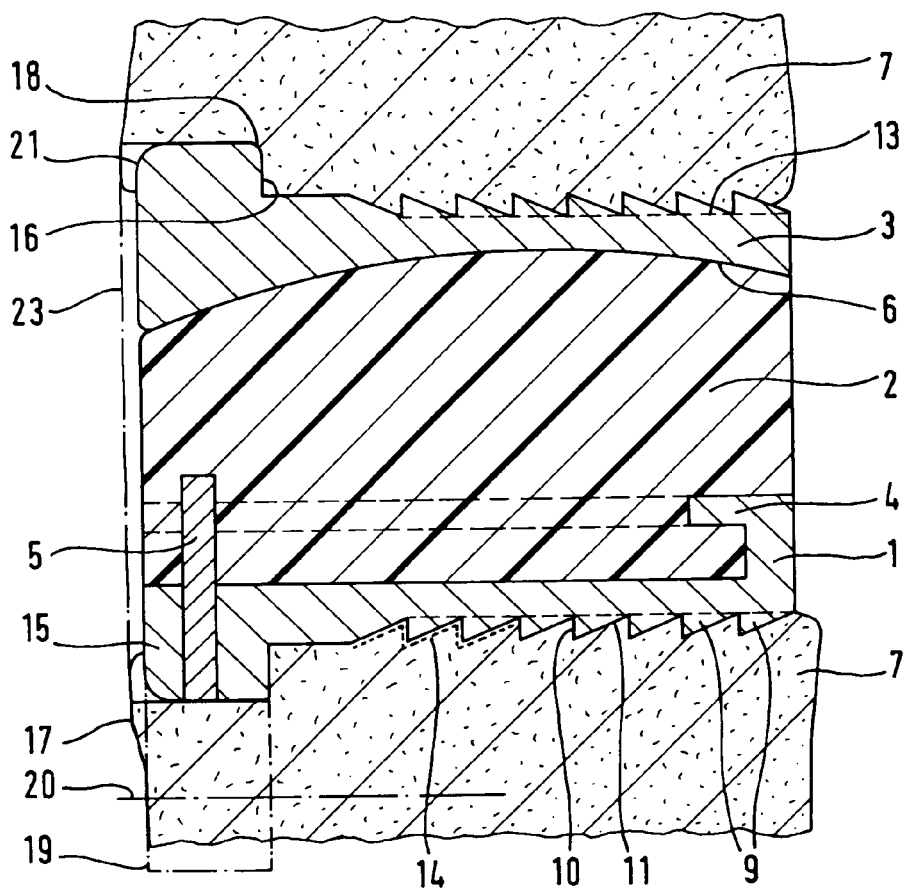
FIG. 3 shows a sagittal section in the scale corresponding to FIG. 2.

At the ventral edge, the cover plates 1, 3 are provided with a ridge-like projection 15 which protrudes in the cranial direction or caudal direction beyond the surface carrying the teeth 9. Because of its mostly planar extent, the projection is also referred to as a flange. For the sake of simplicity, this expression is also used when the projection has only a low height, as can be seen in FIG. 3. Upon implantation, this flange can be positioned such that its dorsally directed abutment surface 16 lies in front of the ventral limit surface 17 of the associated vertebral body 7. However, since, depending on the anatomical circumstances, such an arrangement may entail prosthesis parts protruding ventrally beyond the alignment face 23 of the adjoining vertebral bodies and there causing irritation of the esophagus or other organs, an operating technique is preferred in which the flange 15 (as is shown in FIG. 3) is recessed into the bone. In other words, a small amount of material is worked away at the ventral margin of the vertebral body so that a recess is formed whose shape and size match that of the flange 15 and which receives the flange after implantation. The abutment surface 16 of the flange then lies against the ventral end face of the this recess. In order to permit a tight bearing of the abutment surface 16 on this end face, the edge 18 of the flange can be rounded. So that the bone is not weakened too much, this requires that the flange has only a low height above the surface carrying the teeth 9. This height should be of the order of 0.5 to 2 mm, preferably between 0.8 and 1.3 mm. Expressed in fractions of the maximum dimension of the cover plate in the anteroposterior direction (AP direction), this means preferably 0.5 to 2 tenths.

The low height of the flange has the advantage that the size of the implant is greatly reduced compared to those embodiments in which the flange is provided with fixation members (e.g. screw holes). The reduced dimensions permit implantation through a surgical opening or an insertion channel of correspondingly reduced diameter, for example in endoscopic implantation.

The prosthesis according to the invention affords a very secure fit, in which the serrated teeth, which cause a dorsal "feed direction", prevent unwanted shifting in the ventral direction, while the flange limits the dorsally directed movement of the prosthesis. The position chosen at the time of implantation, in which the abutment surface 16 of the flange 15 bears against a corresponding ventral face of the associated vertebral body, or of the recess formed therein, is thus maintained.

The safety of the prosthesis fit obtained by the teeth 9 depends on the prosthesis being fitted with sufficient pressing between the adjacent vertebral bodies. This pressing is generally sufficient if the posterior longitudinal ligament is retained. If this is not possible, the physician will prefer additional securing with bone screws. For this purpose, a design is provided in which the flanges 15 have a greater height, as is indicated by the dot-and-dash line 19, and contain screw holes which serve to receive a bone screw 20, indicated by dot-and-dash lines. This design may also be recommended if the operating surgeon doubts whether the bone quality is sufficient for securely anchoring the prosthesis solely by means of a press fit and the teeth 9. If the version with the higher flanges is chosen, the physician will generally dispense with embedding this flange in the vertebral body by means of a recess formed in the latter, because the vertebral body could be weakened too much by doing this. Instead, the prosthesis in this case is generally fitted so that the flange comes to lie in front of the ventral face of the vertebra.

In order in each case to avoid or minimize any irritation of adjacent organs, all the edges possibly protruding ventrally beyond the alignment face of the adjacent vertebral bodies are rounded, as can be seen for example at the edge 21.

The toothing 9 of the prosthesis should be so fine that the prosthesis reaches its final position relative to the adjacent vertebral bodies immediately after implantation. In other words, a situation is to be avoided in which at a later stage, during the pressing which takes place between the adjacent vertebral bodies, the teeth sinks to a more than negligible extent with the teeth into the vertebral bodies. This would in fact be associated with an undesired reduction of the cross section of the nerve passages between the vertebrae. In this respect, a height of the teeth of between 0.2 and 0.6 mm, preferably between 0.3 and 0.5 mm, and a spacing of the tooth tips of 0.4 to 2 mm, preferably 0.6 to 1.3 mm, have proven useful.

Figure 2:
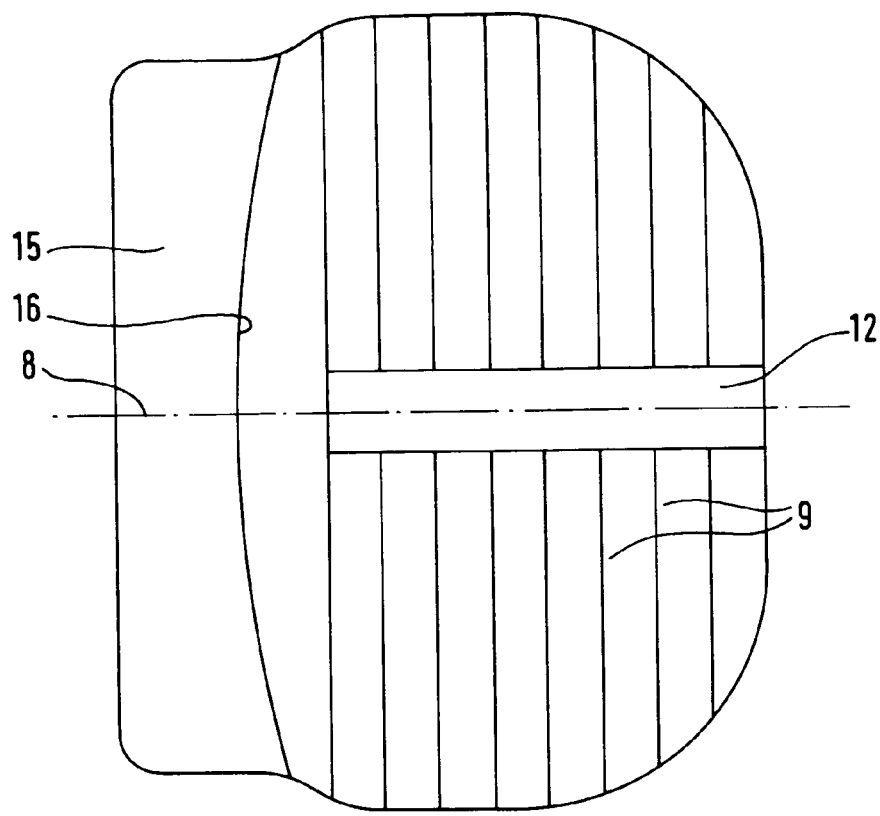
FIG. 2 shows the same on an enlarged scale.

The ventral abutment surface 16 does not have to extend fully across the width of the prosthesis. Instead, it can also be made up of separate, spaced-apart projections expediently arranged symmetrically. Two such projections 22 are indicated in FIG. 1. If a flange-shaped abutment surface 16 is provided, the latter is expediently shaped concavely to match the ventral border of the vertebral bodies, as can be seen in FIG. 2. If the flange has no screw holes and is correspondingly shortened in order to be incorporated into a recess of the vertebral body, a rectilinear abutment surface 16 may however also be expedient, because the end face of the recess cooperating with it can be shaped in any desired way, and a rectilinear formation is particularly simple.

The invention claimed is:

1. A cervical intervertebral prosthesis, comprising two cover plates which are configured to be connected to adjacent vertebral bodies and a prosthesis core,
    wherein at least one of the two cover plates has a toothed portion thereon, the toothed portion having at least one tooth with a steep, ventrally directed flank relative to a vertebral body and a dorsally directed flank relative to a vertebral body, less steep than the ventrally directed flank;
    wherein at least one of the cover plates has, at a ventral edge, a dorsally directed abutment surface formed by a ventral flange configured to cooperate with a ventral surface of a vertebral body, the height of the ventral flange above the surface carrying the toothed portion being 0.5 to 2 mm;
    wherein one of the cover plates has within a guide formed therein a bolt that retains the prosthesis core upon implantation of the cervical intervertebral prosthesis;
    wherein the ventral flange has no screw holes; and
    wherein the slopes of the ventrally and dorsally directed flanks of the at least one tooth and the ventral flange are configured with respect to each other so that in an implanted position the ventral flange prevents movement of the cervical intervertebral prosthesis in a first direction relative to a vertebral body and the at least one tooth prevents movement of the implanted cervical intervertebral prosthesis in a second direction opposite to the first direction.

2. A cervical intervertebral prosthesis, comprising two cover plates which are configured to be connected to adjacent vertebral bodies and a prosthesis core,
    wherein at least one of the two cover plates has a toothed portion thereon which faces toward a vertebral body and which has at least one tooth with a steep, ventrally directed flank relative to the vertebral body and a dorsally directed flank relative to the vertebral body less steep than the ventrally directed flank;
    wherein at least one of the cover plates has at a ventral edge, a dorsally directed abutment surface formed by a ventral flange configured to cooperate with a ventral surface of a vertebral body, the height of the ventral flange being not greater than a fifth of an anterior-posterior dimension of the cover plate;
    wherein one of the cover plates has within a guide formed therein a bolt that retains the prosthesis core upon implantation of the cervical intervertebral prosthesis;
    wherein the ventral flange has no screw holes formed therein; and
    wherein the slopes of the ventrally and dorsally directed flanks of the at least one tooth and the ventral flange are configured with respect to each other so that in an implanted position the ventral flange prevents movement of the cervical intervertebral prosthesis in a first direction relative to a vertebral body and the at least one tooth prevents movement of the implanted cervical intervertebral prosthesis in a second direction opposite to the first direction.

3. The cervical intervertebral prosthesis according to claim 2, wherein the abutment surface is formed by two projections spaced apart from one another and symmetrical with respect to a sagittal center axis of the cover plate.

4. The cervical intervertebral prosthesis according to claim 2, wherein the ventral edges of the cover plates are rounded.

5. A cervical intervertebral prosthesis, comprising two cover plates which are configured to be connected to adjacent vertebral bodies and a prosthesis core,
    wherein at least one of the two cover plates has a toothed portion thereon which faces toward a vertebral body and which has at least one tooth with a steep, ventrally directed flank relative to the vertebral body and a dorsally directed flank relative to the vertebral body less steep than the ventrally directed flank;
    wherein at least one of the cover plates and has, at a ventral edge, a dorsally directed abutment surface formed by two spaced apart projections that are symmetrical with respect to a sagittal cental axis of the cover plate the projections being configured to cooperate with a ventral surface of a vertebral body and having no screwholes formed therein;
    wherein one of the cover plates has within a guide formed therein a bolt that retains the prosthesis core upon implantation of the cervical intervertebral prosthesis; and
    wherein the slopes of the ventrally and dorsally directed flanks of the at least one tooth and the dorsally directed abutment surface are configured with respect to each other so that in an implanted position the dorsally directed abutment surface prevents movement of the cervical intervertebral prosthesis in a first direction relative to a vertebral body and the at least one tooth prevents movement of the implanted cervical intervertebral prosthesis in a second direction opposite to the first direction.

6. The cervical intervertebral prosthesis according to claim 1, 2 or 5, wherein both cover plates have a toothed portion and an abutment surface.

7. The cervical intervertebral prosthesis according to claim 1, 2 or 5, wherein the toothed portion comprises a plurality of teeth with a serrated form, and at least half of the surface directed toward the vertebral body is covered by the toothed portion.

8. The cervical intervertebral prosthesis according to claim 7, wherein substantially the whole of the surface directed toward the vertebral body is covered by the toothed portion.

9. The cervical intervertebral prosthesis according to claim 8, wherein the teeth of the toothed portion extend substantially transversely with respect to a sagittal central axis direction of the prosthesis.

10. The cervical intervertebral prosthesis according to claim 9, wherein the surface directed toward the vertebral body has grooves or ribs which extend transversely with respect to the teeth of the toothed portion.

11. The cervical intervertebral prosthesis according to claim 7, wherein the tooth height is between 0.2 and 0.8 mm.

12. The cervical intervertebral prosthesis according to claim 11, wherein the tooth spacing is between 0.4 and 2 mm.

13. The cervical intervertebral prosthesis according to claim 7, wherein the teeth of the toothed portion extend substantially transversely with respect to a sagittal plane of the prosthesis.

14. The cervical intervertebral prosthesis according to claim 13, wherein the surface directed toward the vertebral body has grooves or ribs which extend transversely with respect to the teeth of the toothed portion.

15. The cervical intervertebral prosthesis according to claim 7, wherein the teeth are provided with a coating which is porous or promotes bone growth.

16. The cervical intervertebral prosthesis according to claim 1, 2 or 5, wherein the ventral flange extends across at least half the width of the cover plate.

17. The cervical intervertebral prosthesis according to claim 1, 2 or 5, wherein the ventral edges of the cover plates are rounded.

18. A method for inserting a cervical intervertebral prosthesis vertebral bodies, comprising:
providing as part of the intervertebral prosthesis two cover plates each cover plate having a toothed portion and a ventral flange having no screw holes formed therein facing in a dorsal direction with respect to each vertebral body;
wherein the toothed portion of each of the cover plates facing toward a vertebral body has at least one tooth with a steep, ventrally directed flank relative to the vertebral body and a dorsally directed flank relative to the vertebral body less steep than the ventrally directed flank;
wherein the slopes of the ventrally and dorsally directed flanks of the at least one tooth and the ventral flange are configured with respect to each other so that in the implanted position the ventral flange prevents movement of the cervical intervertebral prosthesis in a first direction relative to the vertebral body and the at least one tooth prevents movement of the cervical intervertebral prosthesis in a second direction opposite to the first direction;
forming a recess in each of the vertebral bodies with which each of the cover plates cooperates at a ventral margin, each recess receiving the ventral flange of a cover plate; and
dimensioning the depth of the recess in each vertebral body in an anterior-posterior direction with respect to the vertebral body such that no part of the intervertebral prosthesis protrudes beyond the ventral outer surface of the vertebral body; and then inserting the intervertebral prosthesis between the vertebral bodies.

19. The method according to claim 18, further comprising inserting the intervertebral prosthesis endoscopically.

20. The method according to claim 18, wherein the height of the ventral flange above the surface carrying the toothed portion is 0.5 to 2 mm.

21. The method according to claim 18, wherein the height of the ventral flange is not greater than a fifth of an anterior-posterior dimension of the cover plate.

22. A method for implanting a cervical intervertebral prosthesis between vertebral bodies, comprising:
providing as part of the intervertebral prosthesis two cover plates;
at least one cover plate having a toothed portion, a ventral abutment surface on at least one of the cover plates facing in a dorsal direction with respect to a vertebral body and including a dorsally directed abutment surface formed by two spaced apart projections having no screw holes formed therein, the spaced apart projections being symmetrical with respect to a sagittal central axis of the cover plate and configured to cooperate with a ventral surface of the vertebral body, the cover plates being configured to be connected to adjacent vertebral bodies and the toothed portion facing toward a vertebral body and having at least one tooth with a steep, ventrally directed flank relative to the vertebral body and a dorsally directed flank relative to the vertebral body less steep than the ventrally directed flank;
wherein the slopes of the ventrally and dorsally directed flanks of the at least one tooth and the dorsally directed abutment surface are configured with respect to each other so that in an implanted position the dorsally directed abutment surface prevents movement of the cervical intervertebral prosthesis in a first direction relative to a vertebral body and the at least one tooth prevents movement of the implanted cervical intervertebral prosthesis in a second direction opposite to the first direction;
forming a recess in a vertebral body with which a cover plate cooperates at a ventral margin, the recess receiving the projections of the cover plate; and then inserting the intervertebral prosthesis between the vertebral bodies.

* * * * *

UNITED STATES PATENT AND TRADEMARK OFFICE
CERTIFICATE OF CORRECTION

| | | |
|---|---|---|
| PATENT NO. | : 7,267,691 B2 | Page 1 of 1 |
| APPLICATION NO. | : 10/349183 | |
| DATED | : September 11, 2007 | |
| INVENTOR(S) | : Arnold Keller et al. | |

It is certified that error appears in the above-identified patent and that said Letters Patent is hereby corrected as shown below:

In Claim 18, column 7, line 44, insert --between-- in between "prosthesis" and "vertebral."

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,267,691 B1 Page 1 of 1
APPLICATION NO. : 10/349183
DATED : September 11, 2007
INVENTOR(S) : Arnold Keller et al.

It is certified that error appears in the above-identified patent and that said Letters Patent is hereby corrected as shown below:

In Claim 18, column 7, line 44, insert --between-- in between "prosthesis" and "vertebral."

Signed and Sealed this

First Day of January, 2008

JON W. DUDAS
*Director of the United States Patent and Trademark Office*